United States Patent [19]

Skurkovich et al.

[11] Patent Number: 4,824,432
[45] Date of Patent: * Apr. 25, 1989

[54] METHOD FOR TREATING AIDS AND OTHER IMMUNE DEFICIENCIES AND IMMUNE DISORDERS

[75] Inventors: Simon Skurkovich; Boris Skurkovich, both of Rockville, Md.

[73] Assignee: S.V.S. Laboratories, Inc., Rockville, Md.

[ * ] Notice: The portion of the term of this patent subsequent to Dec. 7, 1999 has been disclaimed.

[21] Appl. No.: 843,528

[22] Filed: Mar. 25, 1986

Related U.S. Application Data

[63] Continuation-in-part of Ser. No. 446,680, Dec. 3, 1982, Pat. No. 4,605,394, which is a continuation-in-part of Ser. No. 247,205, Mar. 24, 1981, Pat. No. 4,362,155.

[51] Int. Cl.⁴ .............................................. A61M 37/00
[52] U.S. Cl. .................................... 604/4; 604/49; 424/85.8; 435/811; 436/547; 514/885
[58] Field of Search ................. 424/85, 85.4–85.8, 424/86; 435/811, 172.2; 604/4–6, 49–53; 436/547–548; 530/387, 849, 349, 387; 514/885, 889

[56] References Cited

U.S. PATENT DOCUMENTS

| | | | |
|---|---|---|---|
| 4,009,257 | 2/1977 | Thomas et al. | 424/85 |
| 4,056,614 | 11/1977 | Bonneau et al. | 424/85 |
| 4,165,370 | 8/1979 | Coval | 424/85 |
| 4,168,261 | 9/1979 | Edy | 424/85 |
| 4,172,071 | 10/1979 | De Maeyer et al. | 530/417 |
| 4,215,688 | 8/1980 | Terman et al. | 604/5 |
| 4,362,155 | 12/1982 | Skurkovich | 604/6 |
| 4,381,295 | 4/1983 | Kung et al. | 424/85 |
| 4,414,147 | 11/1983 | Klibanov et al. | 424/85 |
| 4,423,147 | 12/1983 | Secher et al. | 435/811 |
| 4,594,245 | 6/1986 | Yoshida et al. | 424/101 |
| 4,605,394 | 8/1986 | Skurkovich | 604/4 |
| 4,647,773 | 3/1987 | Gallo et al. | 424/89 |
| 4,709,015 | 11/1987 | Kung et al. | 424/85.8 |
| 4,748,018 | 5/1988 | Stolle et al. | 424/86 |

FOREIGN PATENT DOCUMENTS

2725608 1/1978 Fed. Rep. of Germany .......... 604/6

OTHER PUBLICATIONS

Riviere et al, "Inhibitor by Anti-Interferon Serum of Lymphocytic Choriomeningitis Virus Disease in Suckling Mice", May 1977, Proc. Natl. Acad. Sci., 74: 2135–2139.

Annals of N.Y. Academy of Sciences: Acquired Immune Deficiency Syndrome; vol. 437, pp. 65–75, 530–539; Dec. 1984.

Radoiu et al, "Specific Anti-Antibodies", 9/7/71, Specialia, pp. 692–694.

Kawade, "An Analysis of Neutralization Reaction of Interferon by Antibody: A Proposal on the Expression of Neutralization Titer", Fall 1980, vol. 1, #1, pp. 61–70; Journal of Interferon Research.

Gallo, "The AIDS Virus", Scientific American, Jan. 1987, pp. 47–56.

Primary Examiner—C. Fred Rosenbaum
Assistant Examiner—Mario Costantino
Attorney, Agent, or Firm—Gilbert L. Wells

[57] ABSTRACT

Methods are provided for the treatment of pathological conditions connected with the production of interferons which destroy the immune system and possess damaging action on the cell system of mammals. Interferons are removed from the blood of mammals in two general methods. According to the first method antibodies to the interferons are introduced parenterally into the bodies of the mammals. In the second method continuous removal of interferon is achieved for example by extracorporeal perfusion of the blood of the patient through the substances which absorb, adsorb, disintegrate, or inactivate the biological activity of the interferons. HTLV-III/LAV virus is also removed by these methods.

49 Claims, 1 Drawing Sheet

METHOD FOR TREATING AIDS AND OTHER IMMUNE DEFICIENCIES AND IMMUNE DISORDERS

CROSS REFERENCE TO RELATED APPLICATIONS

The present application is a continuation-in-part of application Ser. No. 446,680, filed Dec. 3, 1982, now U.S. Pat. No. 4,605,394 in turn, is a continuation-in-part of application Ser. No. 247,205, filed Mar. 24, 1981, now U.S. Pat. No. 4,362,155.

BACKGROUND OF THE INVENTION

The field of the invention is drug, bio-affecting and body treating compositions and the invention is particularly concerned with interferon (IFN) containing compositions and methods.

The present invention is concerned with the treatment of patients having diseases connected with the hyperproduction or other disturbances of IFN synthesis, including the IFN possessing damaging action on the cells. More particularly, the invention provides methods for treating such patients by removing IFNS from the blood of the patients being treated.

In 1975, IFN was discovered in the blood of patients having autoimmune diseases and allergies. (Annals of Allergy, 35:356, 1975).

In 1980 and 1982 it was reported that the basis for the development of certain diseases (immune deficiencies, such as Acquired Immune Deficiency Syndrome (AIDS), other immune disorders, immune suppression in cancer, and others) can be the disturbances of IFN synthesis with the production of defective types of IFN and IFNs possessing damaging action on cells of organism (Interferon Scientific Memoranda, October 1980, September 1982).

It has also been reported that in the blood of patients having various immune disorders, including AIDS, a pH labile alpha IFN circulates (Second Annual International Cong. for IFN Research, October 1981, J. Infectious Diseases 1982, 146: 451).

Further, it is known that in AIDS and in other immune disorders including cancer and leukemia, besides defective IFNs, immune complexes and blocking antibodies (IgG) also circulate. The production of some of these substances can be stimulated by IFN.

Also, none of the above references is directed to the removal of interferon for the purposes of treating diseases related to hyperproduction of interferon or other disturbances of IFN synthesis, including the production of defective interferon.

In 1974, an article was published setting forth the hypothesis that one of the mechanisms of development of autoimmune diseases is hyperproduction of IFN in a patient's body. (*Nature*, 247:551, Feb. 22, 1974).

An article entitled "Preparation of Monospecific Immunoglobulin Against Human Leukocytic Interferon" was published in the April 1979, *Bulletin of Experimental Biology and Medicine*. This article was primarily directed to the preparation of anti-interferon immunoglobulin for its further use as a substance for the treatment of various autoimmune diseases.

The state of the art of purification of preparations having an IFN type activity may be ascertained by reference to U.S. Pat. Nos. 4,168,261 and 4,172,071, the disclosures of which are incorporated herein by reference.

SUMMARY OF THE INVENTION

The present invention provides for new methods of treatment of diseases and syndromes such as AIDS connected with the disturbance of IFN synthesis, including hyperproduction of interferon (IFN), and, in particular, production of IFN which disintegrates immune regulation and has a damaging action on the cells of organisms. These methods include the use of different agents which bind, disintegrate, or block biological activity of selected interferons and comprise, e.g., antibodies, enzymes, and/or other substances. These agents can be administered into the organism intramuscularly (IM) or intravenously (IV), or used in the apparatus of U.S. Pat. No. 4,362,155 for extracorporeal perfusion where the blood containing IFN is passed through these substances which are immobilized, thus clearing the blood from interferon.

These methods can be used for the treatment of AIDS and other immune deficiencies, and other immune disorders, negative features of aging, immunosupresion in cancers and leukemias, aplastic anemia, autoimmune and allergic diseases in animals and other conditions connected with the negative action of IFNs. It is preferable to administer normal IFNs after the IFNs possessing negative actions are removed.

For the treatment of AIDS and other immune disorders, antibodies to alpha IFN, specifically antibodies to pH labile alpha IFN and antibodies to other types of IFNs or defective IFNs are introduced by IM or IV routes into the patient.

These antibodies can be produced in animals or with the help of the hybridoma methods (monoclonal antibodies in mice or monoclonal antibodies in human lymphocytes).

After the treatment of AIDS patients using antibodies, the patients are further treated with normal gamma IFN, normal beta IFN or interleukin 2(IL-2) combined with gamma IFN.

The development of AIDS is connected with the penetration of the HTLV-III/LAV virus (Science 1984, 224:500) into the organism. Two secondary methods are given to treat and prevent AIDS:

I Immunological method.

A. Immunosorbent Approach

The HTLV-III/LAV virus and microorganisms and other substances which cause oppotunistic infections are removed from an AIDS patient. This method is carried out by passing the blood through an immobilized immunosorbent to the HTLV-III/LAV virus and to microorganisms and other substances which cause opportunistic infections. These immunosorbents include a high concentration of specific antibodies to the HTLV-III/LAV virus and to microorganisms and other substances which cause opportunistic infections. These antibodies include polyclonal antibodies from people whose blood has high titers of antibody to the HTLV-III/LAV virus or microorganisms or other substances which cause opportunistic infections; antibodies from healthy donors or animals who were actively immunized to the HTLV-III/LAV virus or microorganisms or other substances which cause opportunistic infections; and monoclonal antibodies to the virus or microorganisms and other substances which cause opportunistic infections produced in mice hybridoma or in hybridoma with human lymphocytes.

B. High concentrations of specific antibody to HTLVIII/LAV virus are directly administered to AIDS patients. These antibodies include polyclonal antibodies from people whose blood has high titers of antibody to the HTLV-III/LAV virus or microorganisms or other substances which cause opportunistic infections; antibodies from healthy donors or animals who were actively immunized to the HTLV-III/LAV virus or microorganisms or other substances which cause opportunistic infections; and monoclonal antibodies to the virus or microorganisms or other substances which cause opportunistic infections produced in mice hybridoma or in hybridoma with human lymphocytes. These antibodies are also directly administered to people in high risk categories or to people who have reason to believe they are carrying the virus. In the immunosorbent approach or in direct injection the invention contemplates the use of either the antibodies to the HTLV-III/LAV virus alone or the antibodies to the microorganisms or other substances which cause opportunistic infections or both together.

II. Enzyme Disintegration Method

A. The blood of AIDS patients is passed through immobilized enzymes which can disintegrate the HTLV-III/LAV virus, such as RNA nuclease, other enzymes which can disintegrate the viruses which cause opportunistic infections.

B. RNA nuclease which disintegrates the RNA of the virus HTLV-III/LAV, and other RNA or DNA nucleases, or are hostile to viruses which cause opportunistic infections are directly administered parenterally.

The invention contemplates the use of the enzyme method alone or together with the immunological method.

The invention, and its objects and advantages, will become more apparent in the detailed description of the preferred embodiments hereinafter presented.

BRIEF DESCRIPTION OF THE DRAWINGS

In the description of the preferred embodiments of the invention hereinafter presented, reference is made to the accompanying drawings, in which.

DESCRIPTION OF THE PREFERRED EMBODIMENTS

Figure 1:
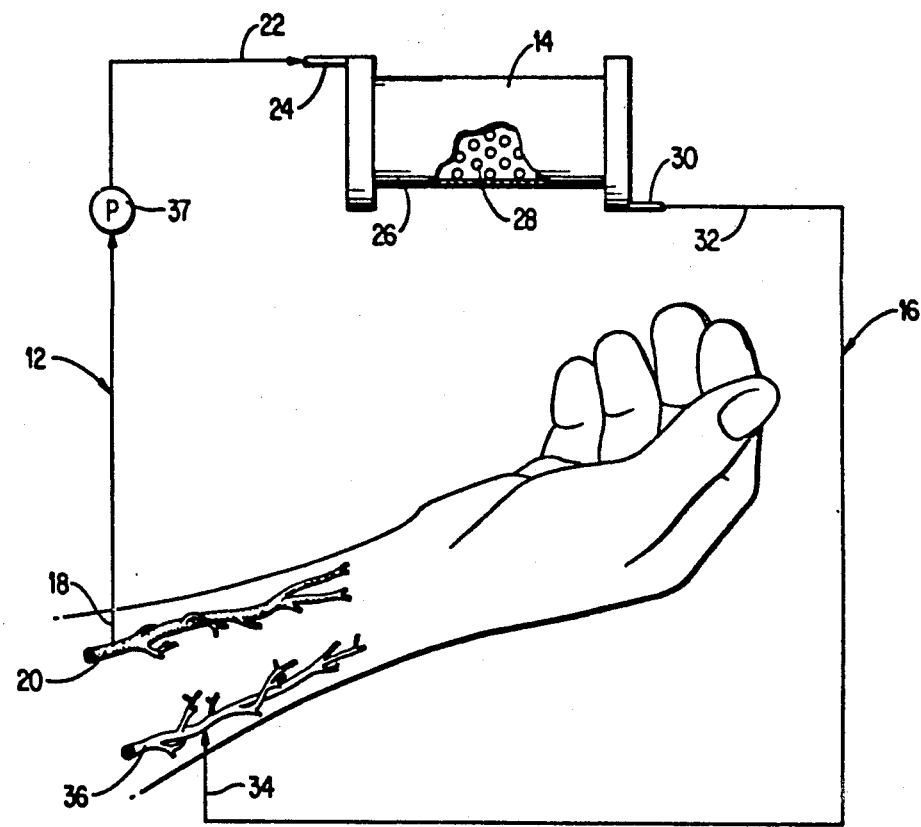
FIG. 1 is a schematic illustration of one embodiment of an apparatus useful in the present invention.

The present invention provides for methods of treatment of diseases and syndromes connected with the hyperproduction of IFNs or other disturbances of IFN synthesis, including the production of defective IFNs which damage the cells of the organism of a patient. Thus, antibodies, enzymes or similarly reacting agents are used for binding, disintegrating or blocking the biological activity of these IFNs. Treatment may be achieved by the administration of the agents into the organism of the patient by IM or IV routes to neutralize or remove the damaging effect of the interferon. The invention preferably uses an apparatus for extracorporeal perfusion where the blood containing interferon is passed through an external reaction chamber containing the above agents and thus the interferon is cleared from the blood.

The present invention provides methods of treatment of AIDS and other immune deficiencies, negative features of aging, immunosuppression in cancers and leukemias, aplastic anemia, autoimmune and allergic diseases in animals, and other conditions connected with the damaging action of IFN.

The invention utilizes apparatus for removing from or disintegrating, or blocking biological activity of interferon in the blood, and for returning blood having a reduced amount or free from interferon to the patient. "Norma" (non-defective) interferon may be introduced to the patient after the completion of the clearance process Hereinafter, the terminology "clearance from interferon" will be used to describe blood that has either a reduced level of interferon or is completely free from interferon by absorption, adsorption, disintegration, inactivation or suppression of the biological activity of interferon. The method is achieved by IM and IV administration of agents into the organism to neutralize or remove the damaging effect of the interferon and by an apparatus preferably in a closed system in which all of the parts are in fluid communication.

During the extracorporeal treatment of a patient, the process of clearance of interferon from the blood is continuous. With this embodiment, the apparatus clears interferon from the whole blood of the patient.

In another embodiment of the invention using the extracorporeal treatment, a method and apparatus are provided in which interferon is cleared from plasma. Alternatively, the interferon is cleared from plasma containing leukocytes. After clearance of interferon, the plasma or plasma with leukocytes, is rejoined with the blood cells or formed elements of the blood and returned to the patient.

Suitable techniques for purifying interferon are described in the aforementioned U.S. Pat. Nos. 4,168,261 and 4,172,071. These techniques are also usable with the present invention for removing interferon. It should be appreciated that the techniques in these references will require minor modifications when used in the present invention.

For the clearance from interferon the present invention uses anti-interferon antibodies, albumin, specific enzymes and other substances capable of absorbing, adsorbing, disintegrating, inactivating or suppressing the biological activity of interferon. A suitable solid support for these substances may be the Sepharose as described in U.S. Pat. No. 4,172,071.

An example of the therapeutic influence on the malignant process is the removal of interferon from an effected organism by the perfusion of the blood through an immunosorbent which contains antibodies to defective interferons, or antibodies to the normal interferons containing common antigenic determinants with defective interferons. Blood cleared from defective interferons is returned to the patient. It is possible to administer normal interferons after the removal of defective interferons.

The following description will be directed in particular to elements forming part of, or cooperating more directly with, the present invention. Elements not specifically shown or described herein are understood to be delectable from those known in the art.

Referring now to the drawings, and to FIG. 1 in particular, one embodiment of an apparatus for treatment of blood to clear interferon is illustrated. The apparatus, which is generally designated 10, comprises an inlet tube 12, means 14 for clearing interferon from blood, and an outlet tube 16. The inlet tube 12 has an inlet end 18 connected to a cannula (not shown) inserted into an artery or blood vessel 20 of a patient. The outlet end 22 of the inlet tube 12 is connected to the inlet 24 of a housing 26 containing a plurality of porous glass beads 28, such as those described in U.S. Pat. No. 4,168,261. The outlet 30 of the housing 26 is connected to an end 32 of the outlet tube 16. The other (outlet) end 34 of tube 16 is connected to a cannula (not shown) inserted into a vein 36 of the patient. Preferably, a pump 37 is included in the apparatus 10. The inlet tube 12 provides means for removing whole blood from a patient, and the outlet tube 16 provides means for returning the blood to the patient. As clearly illustrated in FIG. 1, the tubes 12 and 16 and the means 14 are in continuous fluid communication with each other.

In operation, the cannula connected to the inlet 18 is inserted into the blood vessel of the patient, and the cannula connected to the outlet 34 is inserted into a vein. When a pump is used, the pump is then actuated to pump blood from the patient through the housing 26 so that the beads 28 can remove interferon from the blood. Preferably, all of the interferon is removed from the blood. Blood free from interferon is then returned through the outlet tube 16 into the vein of the patient.

The method used with this embodiment of the invention provides a continuous process for the treatment of conditions connected with the production of defective interferons and conditions connected with the damaging action of IFN. The process involves removing blood from a patient, passing the removed blood through means for clearance of the blood from IFN, and returning the blood, which is free from interferon, to the patient.

Figure 2:
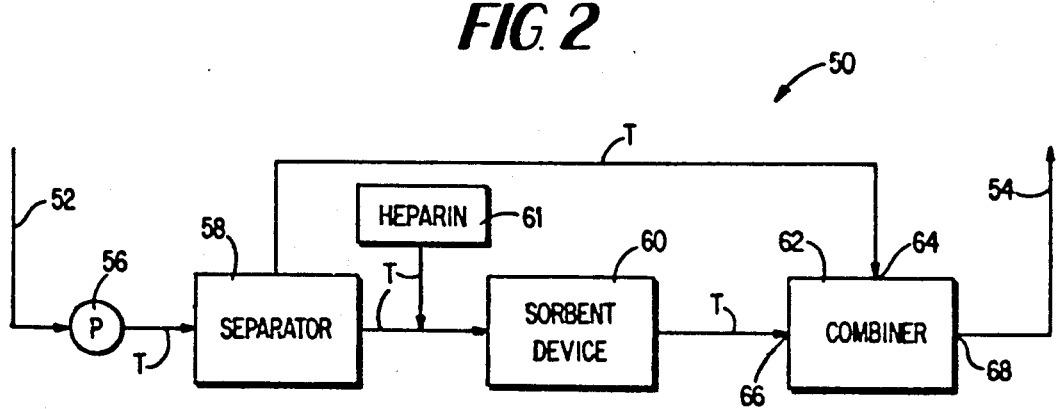
FIG. 2 is a schematic block diagram of another embodiment of an apparatus useful in the present invention.

Referring now to FIG. 2, another embodiment of an apparatus useful in the present invention, generally designated 50, is illustrated. The apparatus 50 includes an inlet tube, generally designated 52, and an outlet tube, generally designated 54. The inlet tube 52 is similar to the inlet tube 12, and the outlet tube 54 is similar to the outlet tube 16 of the embodiment illustrated in FIG. 1. A pump 56 is provided to pump blood from the patient into a separator 58. A suitable separator is a plasma filter of the type described in British Pat. No. 1,562,546. Other suitable methods of plasmapheresis, such as centrifugation, also are usable to separate plasma or plasma with leukocytes from whole blood. The plasma, or plasma with leukocytes, is fed from the separator 58 to a sorbent containing device 60 charged with the aforementioned anti-interferon antibodies. Such a device can be the means 14 for removing interferon described in connection with FIG. 1, in general, a device using a process of the type described in U.S. Pat. No. 4,172,071, or any other suitable method using a capacious sorbent for interferon carried by a solid support. The plasma, or plasma with leukocytes, after passing through the sorbent within the device 60, rejoins the formed elements of blood removed from the whole blood by the separator 58. A combiner 62 is illustrated for providing the mixing function. Such a combiner need be no more complex than a mixing valve having one inlet 64 connected to the separator 58 and a second inlet 66 connected to the device 60. The outlet 68 of the valve is connected to the outlet tube 54. A device 61 for adding heparin to the plasma, or plasma with leukocytes, is positionable between the separator 58 and the device 60. Sections of tubing T interconnect the pump 56, the separator 58, the device 60, the device 61, and the combiner 64, as illustrated in FIG. 2. Thus, the various components of the apparatus 50 are in fluid communication with each other.

The method of clearing blood for treating diseases and conditions connected with the production of defective IFNs and connected with damaging action of IFN utilizing the apparatus of FIG. 2 involves the connection of the inlet and outlet tubes to a blood vessel and a vein, respectively, of a patient to be treated; pumping the whole blood of the patient to a separator; separating plasma, or plasma with leukocytes, from blood cells within the separator; passing the plasma, or plasma with leukocytes, through a device for clearing interferon; combining the plasma, or plasma with leukocytes, after clearance of interferon, with the previously removed blood cells; and returning the combined blood to the patient.

In a modification of this embodiment, the separator device separates the blood into plasma (or plasma with leukocytes), and other blood cells. The plasma (or plasma with leukocytes) is processed as previously described.

In another modification, the device 60 utilizes a combined sorbent having a first component for absorbing interferon from the plasma or plasma with leukocytes and a second component that selectively absorbs blocking antibodies in cases of cancers and leukemias, from the plasma or plasma with leukocytes being treated. The particular component is a function of the disease or condition being treated. By utilizing a combined sorbent, the effectiveness of the invention is enhanced.

SPECIFIC EXAMPLES

The following specific examples further illustrate the present invention.

EXAMPLE 1

Preparation of the anti-alpha interferon antibodies.

Sheep were immunized weekly or bi-weekly with purified human alpha interferon. Following the development of high titer anti-alpha interferon serum antibodies, the animals received a booster injection of interferon. Seven to fourteen days after the booster, when anti-alpha interferon titer was maximal, the immune plasma was collected by plasmapheresis and anti-interferon immunoglobulin was isolated by affinity chromatography. The immunoglobulin was aliquoted in ampules of 1–3 milliliters each and stored as liquid at 2°–8° C. Anti-interferon antibody activity was determined by a neutralization method. Contaminating antibodies (cross-reactivity antibodies) were detected by the ELISA method.

Starting with the immune plasma from sheep the following steps were carried out:

1. Sheep immune plasma was reacted with 25% human serum albumin (HSA) (to a final concentration of 0.5% HSA) for 18 hours at 4° C.

2. Sterile saturated ammonium sulfate was added to a final concentration of 20% and reacted 30 minutes at room temperature.

3. This was centrifuged at 7000 g for 30 minutes and the supernatant was removed.

4. Saturated ammonium sulfate was added to the supernatant to a final concentration of 45% and reacted 30 minutes at room temperature.

5. This was centrifuged at 7000 g for 30 minutes and the supernatant was discarded.

6. The pellet was dissolved in 0.05 Tris/HCl, 0.05M NaCl, pH 8.0 to one third of the starting plasma volume and then was dialyzed against 20 volumes of the same buffer overnight with 3 changes of buffer.

7. The dialyzed material was absorbed through a Blue Sepharose (Cl-68 (Pharmacia) column containing human serum albumin, and chicken ovalbumen equilibrated in 0.05M Tris/HCl, 0.05 M NaCl, pH 8.0 buffer at 4° C.

8. The protein fall-through from the column was then placed through an Affi-Gel 10 (BioRad Inc., Richmond, Calif.) coupled with human leukocyte membrane extracts and normal human serum (hepatitis B negative) equilibrated with 0.05M Tris/HCl, 0.05M NaCl, pH 8.0 buffer.

9. The fall-through was dialyzed against 20 columns 0.01 M sodium phosphate buffer 3×pH 6.4 in 24 hours and applied to a DEAE cartridge (American Fluid Conditioning Co., Zek Prep).

10. The fall-through peak was collected and concentrated in an Amicon concentrator with a XM-100 membrane to a concentration of 30 mg/ml and sterile filtered through a 0.22 μm filter.

11. The concentrated immunoglobulin was passed through a Detoxigel column (Pierce Chemical Co.) twice to remove any traces of endotoxin.

12. The fall-through fraction from the Detoxigel column was sterile filtered through a 0.22 μm filter and bottled in sterile pyrogen free bottles.

The sheep anti-alpha interferon immunoglobulin obtained as above is administered parenterally (IM or IV) to patients having AIDS at a dose of 16,000-25,000 units/Kg of body weight two to three times per day.

EXAMPLE 2

Anti-alpha human IFN obtained as in Example 1, is given IM or IV. Four or five hours later human gamma IFN is administered in doses of $1\text{–}3\times10^6$ IU during the treatment with antibody.

EXAMPLE 3

This example is carried out as in Example 2, but IL-2 is given in addition every day during treatment with antibody 4–6 hours after administration of the antibody in doses of approximately 10,000–150,000 or greater IU/Kg intravenously. Then one hour after this, gamma IFN is administered IM as in Example 1.

EXAMPLE 4

Sheep are immunized with very pure human IgG (from Calbiochem Corp.) as in Example 1. Immune plasma is collected using plasmapheresis as in Example 1 and the antibody to IgG is isolated using the affinity chromatography method. The antibody to IgG is used either in the form of an injection or as an immunosorbent in the apparatus of FIG. 2 to remove IgG or immune complexes which contain IgG from patients having cancers or other immune disorders in mammals.

EXAMPLE 5

Protein A (Pharmacia) is used as an immunosorbent in the apparatus of FIG. 2 to remove IgG or immune complexes which contain IgG from patients having cancers or other immune disorders in mammals.

EXAMPLE 6

The immune plasma collected in Example 1 and the immunoglobulin isolated from the plasma is administered parenterally (IM or IV) to patients having cancers or other immune disorders in mammals.

EXAMPLE 7

Sheep are immunized with inactivated HTLV-III/-LAV. Immune plasma is collected using plasmapheresis as in Example 2 and the antibodies to HTLV-III/LAV are isolated by affinity chromotography. The antibodies to HTLV-III/LAV are used either in the form of an injection or as an immunosorbent in the apparatus of FIG. 2 to remove HTLV-III/LAV from patients having AIDS.

EXAMPLE 8

Antibodies to HTLV-III/LAV are obtained from people having high titers of these antibodies or from donors who were immunized with HTLV-III/LAV virus. Plasma is collected and used as in Example 7.

EXAMPLE 9

RNA nuclease is used as an immobilized enzyme in the apparatus of FIG. 2 to disintegrate the HTLV-III/-LAV virus present in the blood of AIDS patients.

EXAMPLE 10

RNA nuclease is directly administered parenterally to AIDS patients to disintegrate the RNA of the HTLV-III/LAV virus.

What is claimed is:

1. In the method of treatment of mammals having immunodeficiencies associated with the disturbance of the synthesis of interferons and the production of defective intererons, the improvement comprising parenterally administering to the body thereof a therapeutic amount of inteferon clearing agent to clear said defective interferons from said body.

2. In the method of treatment of mammals having immunodisorders associated with the disturbance of the synthesis of interferons and the production of defective interferons, the improvement comprising parenterally administering to the body thereof a therapeutic amount of interferon clearing agent to clear said defective interferons from said body.

3. In the method of treatment of humans having a acquired immune deficiency syndrome associated with the disturbance of the synthesis of interferons and the production of defective inteferons, the improvement comprising parenterally administering to the body thereof a therapeutic amount of interferon clearing agent to clear said defective interferons from said body.

4. In the method of treatment of humans having acquired immune deficiency syndrome, the movement comprising parenterally administering to the body thereof a therapeutic amount of RNA nuclease.

5. In the method of treatment of humans having acquired immune deficiency syndrome, the improvement comprising parenterally administering to the body thereof a therapeutic amount of antibody to HTLV-III/LAV.

6. The method of claim 1, wherein said defective inteferons comprise alpha interferon and said alpha interferon is cleared from said body.

7. The method of claim 6, wherein said interferon clearing agent is an antibody to alpha interferon.

8. The method of claim 2, wherein said defective inteferons comprise alpha interferon and said alpha interferon is cleared from said body.

9. The method of claim 8, wherein said interferon clearing agent is an antibody to alpha interferon.

10. The method of claim 3, wherein said defective interferons comprise alpha interferon and said alpha interferon is cleared from said body.

11. The method of claim 10, wherein said interferon clearing agent is an antibody to alpha interferon.

12. The method of claim 1, wherein said defective inteferons comprise pH labile alpha interferon and said pH labile interferon is cleared form said body.

13. The method of claim 12, wherein said interferon clearing agent is an antibody to pH labile alpha interferon.

14. The method of claim 2, wherein said defective inferons comprise pH labile alpha interferon and said pH labile inteferon is cleared from said body.

15. The method of claim 14, wherein said interferon clearing agent is an antibody to pH alpha interferon.

16. The method of claim 3, wherein said defective interferons comprise pH labile alpha interferon and said pH labile alpha interferon is cleared form said body.

17. The method of claim 16, wherein said interferon clearing agent is an antibody to pH alpha interferon.

18. The method of claim 1, further comprising IgG in said body, a clearing agent for said IgG and said IgG is cleared from said body.

19. The method of claim 2, further comprising IgG in said body, a clearing agent for said IgG and said IgG is cleared from said body.

20. The method of claim 3, further comprising Igg in said body, a clearing agent for said IgG and said IgG is cleared from said body.

21. The method of claim 9, further comprising the parenteral administration of gamma interferon.

22. The method of claim 15, further comprising the parenteral administration of gamma interferon.

23. The method of claim 9, further comprising the parenteral adminstration of beta interferon.

24. The method of claim 15, further comprising the parenteral administration of beta interferon.

25. The method of claim 9, further comprising the parenteral administration of interleukin 2 and gamma interferon.

26. The method of claim 9, further comprising the parenteral administration of interleukin 2 and gamma inteferon.

27. In the method of treatment of mammals having immunodisorders associated with the disturbance of the synthesis of interferons and the production of defective interferons, the improvement comprising selectively removing blood from the body thereof, contacting the removed blood with an immunosorbent for said defective interferons, removing said defective interferons on said immunosorbent and returning said blood free of defective interferons to said body.

28. In the method of treatment of humans having acquired immune deficiency syndrome associated with the disturbance of the synthesis of interferons and the production of defective interferons, the improvement comprising selectively removing blood from the body thereof, contacting the removed blood with an immunosorbent for said defective inteferons, removing said defective intererons on said immunosorbent and returning said blood free of defective interferons to said body.

29. The method of claim 27, wherein said defective interferons comprises alpha interferon and said alpha interferon is cleared from said body.

30. The method of claim 29, wherein said immunosorbent is an anitbody to alpha inteferon.

31. The method of claim 27, wherein said defective interferon comprises pH labile alpha interferon and said pH labile alpha interferon is cleared from said body.

32. The method of claim 31, wherein said immunosorbent is an antibody to pH labile alpha interferon.

33. The method of claim 27, further comprising IgG in said body, a clearing agent for said IgG and said IgG is cleared from said body.

34. In a method of treating diseases comprising the step of selectively clearing the blood of a patient from defective interferons using an apparatus having, in continuous fluid communication, an inlet tube, absorbing means for absorbing and thereby removing defective interferons from the whole blood, and an outlet tube, said method comprising:

connecting the inlet tube of said apparatus to a blood vessel of a patient and connecting the outlet tube of said apparatus to a vein of the patient;

removing blood form the blood vessel of the patient;

passing the removed blood through the absorbing means for absorbing defective interferons to thereby remove the amount of interferons in the blood; and returning the blood to the vein of the patient, the improvement comprising:

the step of administering normal inteferon to said patient, said step of administering taking place after the blood has been cleared and returned to the patient and is no longer being removed from the patient.

35. In a method of treating diseases comprising the step of selectively clearing the blood of a patient from defective inteferons using an apparatus having, in continuous fluid communication, an inlet tube, absorbing means for absorbing and thereby removing defective interferons from the whole blood, and an outlet tube, said method comprising:

connecting the inlet tube of said apparatus to a blood vessel of a patient and connecting the outlet tube of said apparatus to a vein of the patient;

removing blood from the blood vessel of the patient;

separating the removed blood into blood cells and plasma;

passing the plasma through the absorbing means for absorbing interferons to thereby remove interferons within the plasma;

combining the plasma having interferons removed with the blood cells previously removed from the blood; and returning the combined blood cells and plasma to the patient;

the improvement comprising:

the step of administering normal interferon to said patient, said step of administering taking pace after the blood has been cleared and returned to the patient and is no longer being removed from the patient.

36. The method of claim 1, wherein said interferon clearing agent is an interferon disintegrating enzyme.

37. The method of claim 2, wherein said interferon clearing agent is an interferon disintegrating enzyme.

38. The method of claim 3, wherein said interferon clearing agent is an interferon disintegrating enzyme.

39. The method of claim 28, further comprising adding an immunosorbent to HTLV-III/LAV to said removed blood.

40. The method of claim 28, further comprising adding an immunosorbent to microorganisms which cause opportunistic infections to said removed blood.

41. The method of claim 28, further comprising said immunosorbent containing RNA nuclease.

42. The method of claim 41, further comprising said immunosorbent containing DNA nuclease.

43. The method of claim 28, wherein said immunosorbent is an immunosorbent to both HTLV-III/-LAV virus and microorganisms which cause opportunistic infections.

44. The method of claim 3, further comprising parenteral administration of antibody to HTLV-III/LAV virus.

45. The method of claim 3, further comprising parenteral administration of antibodies to microorganisms which cause opportunistic infections.

46. The method of claim 3, further comprising parenteral administration of antibodies to both HTLV-III/-LAV virus and microorganisms which cause opportunistic infections.

47. The method of claim 4, further comprising the parenteral administration of DNA nuclease.

48. In the method of treatment of humans having acquired immune deficiency syndrome, the improvement comprising selectively removing blood from the body thereof, contacting the removed blood with an immunosorbent for HTLV-III/LAV, removing said HTLV-II/LAV on said immunosorbent and returning said blood free of HTLV-III/LAV to said body.

49. In the method of treatment of humans having been exposed to the HTLv-III/LAv virus, the improvement comprising parenterally administering to the body thereof a therapeutic amount of antibody to HTLV-III/LAV.

* * * * *